US012746303B2

(12) United States Patent
Wang et al.

(10) Patent No.: US 12,746,303 B2
(45) Date of Patent: Sep. 29, 2026

(54) ADSORPTIVE DEODORIZING MATERIALS, PREPARATION METHODS, AND AIR PURIFICATION DEVICES

(71) Applicant: GUANGDONG ERACLEAN TECHNOLOGY CO., LTD., Zhongshan (CN)

(72) Inventors: Jian Wang, Foshan (CN); Zhiyong Liang, Zhongshan (CN)

(73) Assignee: GUANGDONG ERACLEAN TECHNOLOGY CO., LTD., Zhongshan (CN)

( * ) Notice: Subject to any disclaimer, the term of this patent is extended or adjusted under 35 U.S.C. 154(b) by 0 days.

(21) Appl. No.: 19/380,926

(22) Filed: Nov. 5, 2025

(65) Prior Publication Data

US 2026/0256972 A1 Sep. 3, 2026

(30) Foreign Application Priority Data

Feb. 28, 2025 (CN) ......................... 202510236313.5

(51) Int. Cl.
*A61L 9/00* (2006.01)
*A61L 9/014* (2006.01)
(Continued)

(52) U.S. Cl.
CPC ........... *A61L 9/014* (2013.01); *B01J 20/0222* (2013.01); *B01J 20/0225* (2013.01);
(Continued)

(58) Field of Classification Search
CPC . A61L 2/022; A61L 2/23; A61L 2/235; A61L 9/014; A61L 2101/16;
(Continued)

(56) References Cited

U.S. PATENT DOCUMENTS

| | | | | |
|---|---|---|---|---|
| 4,399,052 A * | 8/1983 | Sugino | C01B 32/382 | 428/116 |
| 4,619,948 A * | 10/1986 | Kennedy | C08J 9/02 | 425/816 |

(Continued)

FOREIGN PATENT DOCUMENTS

CN 1765421 A 5/2006

*Primary Examiner* — Monzer R Chorbaji
(74) *Attorney, Agent, or Firm* — PORUS IP LLC

(57) ABSTRACT

Provided are an adsorptive deodorizing material, a preparation method, and an air purification device. The adsorptive deodorizing material includes activated carbon powder, deionized water, a manganese compound, a soluble copper salt, phosphoric acid, and a soluble nickel salt. By using the phosphoric acid to adjust the acidity and alkalinity of a surface of a porous carrier, the acidity of the surface of the porous carrier is enhanced, which can increase the adsorption capacity of the porous carrier for alkaline odors and acidic odors, thereby accelerating decomposition and conversion of odors and enhancing a deodorizing capability of the adsorptive deodorizing material. In the preparation method, the activated carbon powder is first mixed with a portion of a chemical agent, followed by molding, sintering, and soaking in a remaining chemical agent. This process enables the adsorptive deodorizing material to maintain a good deodorizing capability for a long time.

12 Claims, 1 Drawing Sheet

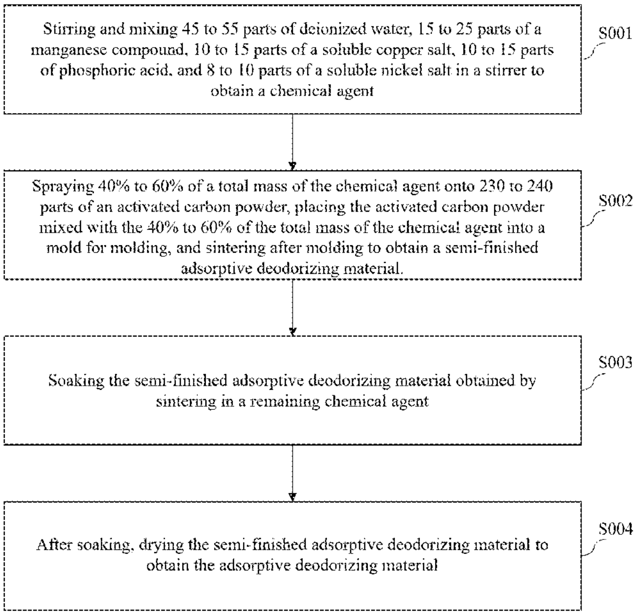

(51) Int. Cl.

| | |
|---|---|
| ***A62B 7/08*** | (2006.01) |
| ***B01J 20/02*** | (2006.01) |
| ***B01J 20/20*** | (2006.01) |
| ***B01J 20/28*** | (2006.01) |
| ***B01J 20/32*** | (2006.01) |
| ***B32B 3/12*** | (2006.01) |

(52) U.S. Cl.

CPC ........... *B01J 20/0237* (2013.01); *B01J 20/20* (2013.01); *B01J 20/28045* (2013.01); *B01J 20/3204* (2013.01); *A61L 2209/22* (2013.01)

(58) Field of Classification Search

CPC ............. A61L 2101/26; A61L 2101/02; A61L 2209/22; C08J 9/24; B01J 20/28045

USPC ...... 422/5, 122, 123, 211; 425/816; 428/116

See application file for complete search history.

(56) References Cited

U.S. PATENT DOCUMENTS

2018/0272260 A1* 9/2018 Robertson .................. C08J 9/24
2020/0384416 A1* 12/2020 Omatsu .................. B01D 61/18

* cited by examiner

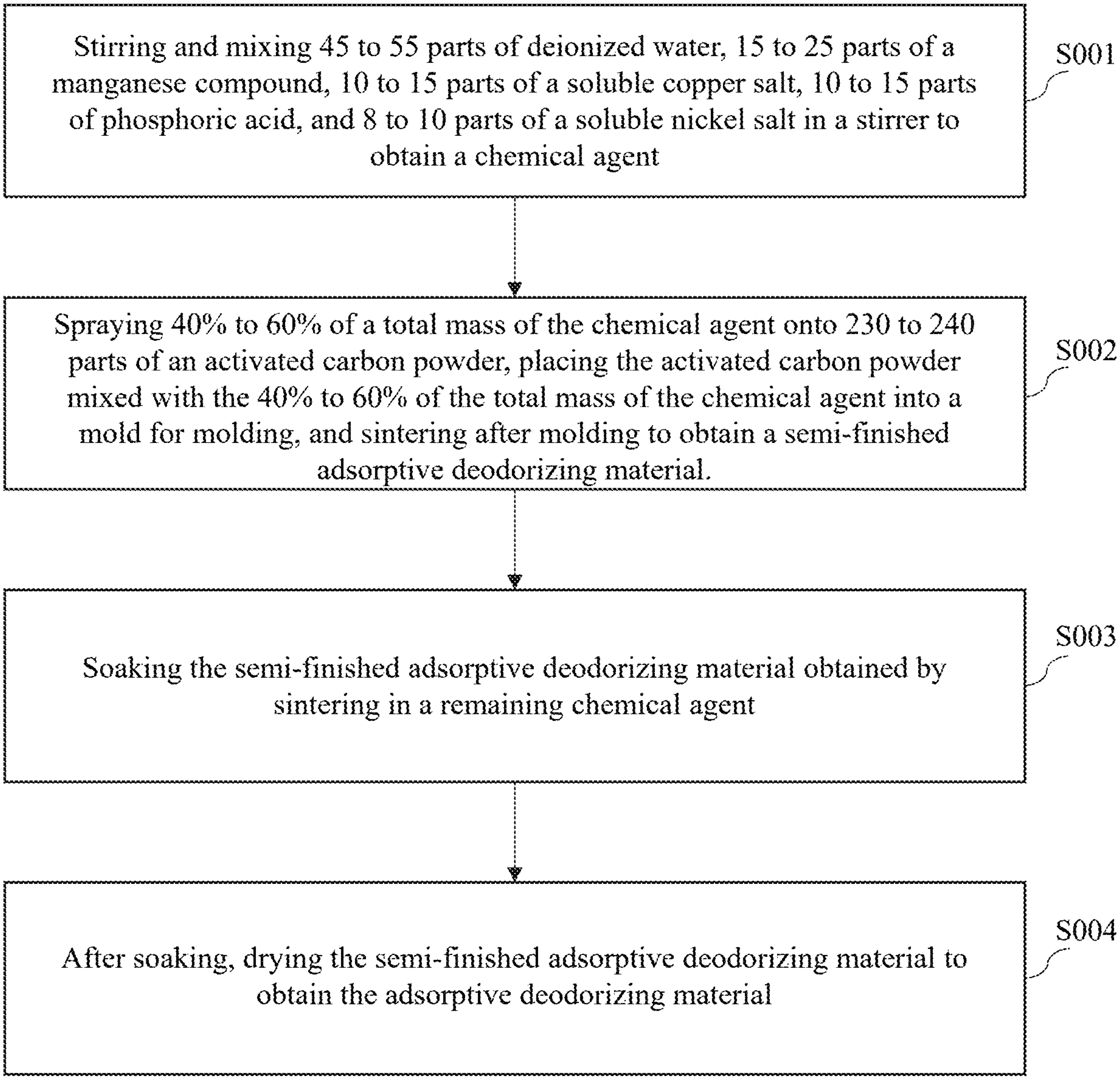
Stirring and mixing 45 to 55 parts of deionized water, 15 to 25 parts of a manganese compound, 10 to 15 parts of a soluble copper salt, 10 to 15 parts of phosphoric acid, and 8 to 10 parts of a soluble nickel salt in a stirrer to obtain a chemical agent
S001
Spraying 40% to 60% of a total mass of the chemical agent onto 230 to 240 parts of an activated carbon powder, placing the activated carbon powder mixed with the 40% to 60% of the total mass of the chemical agent into a mold for molding, and sintering after molding to obtain a semi-finished adsorptive deodorizing material.
S002
Soaking the semi-finished adsorptive deodorizing material obtained by sintering in a remaining chemical agent
S003
After soaking, drying the semi-finished adsorptive deodorizing material to obtain the adsorptive deodorizing material
S004

ADSORPTIVE DEODORIZING MATERIALS, PREPARATION METHODS, AND AIR PURIFICATION DEVICES

CROSS-REFERENCE TO RELATED APPLICATIONS

This application claims priority to the Chinese Patent Application No. 202510236313.5, filed on Feb. 28, 2025, the contents of which are hereby incorporated by reference.

TECHNICAL FIELD

The present disclosure relates to the technical field of adsorptive deodorizing materials, and in particular to an adsorptive deodorizing material, a preparation method, and an air purification device.

BACKGROUND

To further improve the quality of life, people are no longer satisfied with only removing formaldehyde, VOCs, and particulate matter from indoor air, and have put forward requirements for the removal of common odors in daily life. Components of the common odors in the daily life include nitrogen-containing compounds such as ammonia and trimethylamine, sulfur compounds such as hydrogen sulfide and methyl mercaptan, and acidic substances such as acetic acid.

Chinese Patent Application (Publication No. CN1765421A) discloses a method for manufacturing a room-temperature catalytic deodorizing material. The method includes dissolving a main catalyst and an auxiliary catalyst in distilled water, stirring to prepare a catalyst, soaking a porous carrier material in the catalyst, lifting the porous carrier material, air-drying at a room temperature or drying at a low temperature, and performing molding processing according to specifications required for equipment such as refrigerators and air conditioners to obtain the room-temperature catalytic deodorizing material. However, in the above-mentioned room-temperature catalytic deodorizing material, an acidity on a surface of the porous carrier material is relatively weak. For alkaline odors, when a pH value on the surface of the porous carrier material is relatively high, an adsorption effect of the porous carrier material is affected, indicating that the deodorization capability of such materials still requires enhancement.

In view of this, the present disclosure provides an adsorptive deodorizing material, a preparation method, and an air purification device to solve a problem in existing room-temperature catalytic deodorizing materials where the acidity on the surface of the porous carrier material is relatively weak and an adsorption effect for the alkaline odors is poor.

SUMMARY

One or more embodiments of the present disclosure provide an adsorptive deodorizing material, including: in parts by weight, 230 to 240 parts of activated carbon powder, 45 to 55 parts of deionized water, 15 to 25 parts of a manganese compound, 10 to 15 parts of a soluble copper salt, 10 to 15 parts of phosphoric acid, and 8 to 10 parts of a soluble nickel salt; the phosphoric acid is industrial phosphoric acid with a purity of 85%.

One or more embodiments of the present disclosure provide a preparation method for the adsorptive deodorizing material, including: stirring and mixing the deionized water, the manganese compound, the soluble copper salt, the phosphoric acid, and the soluble nickel salt in a stirrer to obtain a chemical agent; spraying 40% to 60% of a total mass of the chemical agent onto the activated carbon powder, stirring and mixing, placing the activated carbon powder mixed with the 40% to 60% of the total mass of the chemical agent into a mold for molding, and sintering after molding to obtain a semi-finished adsorptive deodorizing material; soaking the semi-finished adsorptive deodorizing material in a remaining chemical agent; and after soaking, drying the semi-finished adsorptive deodorizing material to obtain the adsorptive deodorizing material.

The present disclosure further provides an air purification device including the adsorptive deodorizing material.

BRIEF DESCRIPTION OF THE DRAWINGS

To more clearly illustrate the technical solutions in the embodiments of the present disclosure or related technologies, the drawings used in the description of the embodiments or the related technologies are briefly introduced below. Obviously, the drawings in the following description are only some embodiments of the present disclosure. For those skilled in the art, other drawings may be obtained based on the following drawings without any inventive effort.

FIG. 1 is a flowchart illustrating an exemplary preparation method for an adsorptive deodorizing material according to some embodiments of the present disclosure.

DETAILED DESCRIPTION

The technical solutions in the embodiments of the present disclosure are clearly and completely described below in conjunction with the drawings in the embodiments of the present disclosure. The embodiments described are merely some embodiments of the present disclosure, rather than all embodiments. All other embodiments obtained by those skilled in the art based on the embodiments of the present disclosure without inventive efforts shall fall within the scope of the present disclosure.

Some embodiments of the present disclosure provide an adsorptive deodorizing material, including: in parts by weight, 230 to 240 parts of activated carbon powder, 45 to 55 parts of deionized water, 15 to 25 parts of a manganese compound, 10 to 15 parts of a soluble copper salt, 10 to 15 parts of phosphoric acid, and 8 to 10 parts of a soluble nickel salt. The phosphoric acid is industrial phosphoric acid with a purity of 85%.

The activated carbon powder is used to form a porous carrier. The porous carrier may load a catalyst with a deodorizing function (e.g., the manganese compound, the soluble copper salt, or the soluble nickel salt) in pores or on a surface of the porous carrier. This enables the porous carrier to not only adsorb odor molecules but also catalyze a chemical reaction of the odor molecules, converting the odor molecules into harmless substances and thereby enhancing deodorization efficiency.

In some embodiments, the activated carbon powder in the adsorptive deodorizing material may be 230 to 235 parts by weight.

In some embodiments, the activated carbon powder in the adsorptive deodorizing material may be 235 to 240 parts by weight.

In some embodiments, the activated carbon powder in the adsorptive deodorizing material may be 230 parts, 233 parts, 235 parts, 238 parts, or 240 parts by weight.

In some embodiments, the activated carbon powder in the adsorptive deodorizing material has a particle size of 200 to 400 mesh.

In some embodiments, the activated carbon powder in the adsorptive deodorizing material has a particle size of 300 mesh.

In some embodiments, the activated carbon powder in the adsorptive deodorizing material has a particle size of 200 mesh, 250 mesh, 300 mesh, 350 mesh, or 400 mesh.

In some embodiments, the activated carbon powder in the adsorptive deodorizing material has a particle size of 200 to 240 mesh, 240 to 290 mesh, 290 to 330 mesh, or 330 to 400 mesh.

When the particle size of the activated carbon powder in the adsorptive deodorizing material is in a range of 200 to 400 mesh, the activated carbon powder accumulates to form more and finer interparticle voids during a process of pressing the porous carrier. The interparticle voids are connected to micropores of the activated carbon, creating an air-permeable network within the porous carrier. As a result, more diffusion paths are provided for air molecules, thereby improving an air permeability. When the air permeability of the porous carrier is improved, a contact opportunity between the odor molecules and the surface of the porous carrier is greatly enhanced, thereby further improving an adsorption capacity of odors by the porous carrier.

In some embodiments, when the particle size of the activated carbon powder in the adsorptive deodorizing material is greater than 400 mesh, the activated carbon powder is too fine and tends to agglomerate. The agglomeration reduces the interparticle voids, thereby decreasing the air permeability of the porous carrier and adversely affecting the adsorption capacity of the odors by the porous carrier.

The manganese compound includes a compound that is soluble in a solvent to form corresponding manganese ions, or a compound that reacts with malodorous substances such as hydrogen sulfide or ammonia. In some embodiments, the manganese compound may be at least one of manganese oxide, manganese chloride, or manganese sulfate. The manganese compound may be loaded in the pores or on the surface of the porous carrier. The manganese ions in the manganese compound may exist in a plurality of valence states, such as $Mn^{2+}$ and $Mn^{4+}$. During a deodorizing process, the manganese ions participate in redox reactions through a conversion between different valence states. For example, $Mn^{4+}$ oxidizes sulfur components in the odors into elemental sulfur, while $Mn^{4+}$ itself is reduced to $Mn^{2+}$. The $Mn^{2+}$ then is oxidized by oxygen to $Mn^{4+}$, allowing a cycle to continue and enabling a continuous decomposition of a sulfide in the odors. In addition, the manganese ions may react with oxygen or water molecules in air to generate reactive oxygen species such as hydroxyl radicals or hydrogen peroxide. The reactive oxygen species possess strong oxidizing abilities and can rapidly react with organic components in the odors, decomposing the organic components into harmless small molecules such as carbon dioxide and water.

In some embodiments, the manganese compound in the adsorptive deodorizing material may be 15 to 20 parts by weight.

In some embodiments, the manganese compound in the adsorptive deodorizing material may be 20 to 25 parts by weight.

In some embodiments, the manganese compound in the adsorptive deodorizing material may be 15 parts, 17 parts, 20 parts, 22 parts, or 25 parts by weight.

In some embodiments of the present disclosure, using the manganese compound as a component of the adsorptive deodorizing material can effectively promote an oxidative decomposition of organic substances, showing particularly significant removal effects on malodorous compounds containing sulfur or nitrogen. Different forms of the manganese compounds, such as the manganese oxide, the manganese chloride, or the manganese sulfate, may be selected according to specific application requirements to provide diverse catalytic activities and enhance the deodorizing performance of the adsorptive deodorizing material.

The soluble copper salt refers to a compound that is soluble in water or other solvents to form corresponding copper ions. In some embodiments, the soluble copper salt may include at least one of copper chloride, copper sulfate, or copper nitrate. The copper salt provides active sites on the surface of the porous carrier. When the sulfide or other odors contacts the surface of the porous carrier, $Cu^{2+}$ attracts the sulfide, enriching the sulfide near the active sites and increasing a reaction probability. In addition, the copper salt participates in a redox reaction to decompose malodorous substances. $Cu^{2+}$ oxidizes sulfur in the sulfide while $Cu^{2+}$ itself is reduced to Cut, which then is oxidized back to $Cu^{2+}$ in a presence of oxygen, allowing a cycle to continue and enabling a continuous catalytic decomposition of the odors.

In some embodiments, the soluble copper salt in the adsorptive deodorizing material may be 10 to 12 parts by weight.

In some embodiments, the soluble copper salt in the adsorptive deodorizing material may be 12 to 15 parts by weight.

In some embodiments, the soluble copper salt in the adsorptive deodorizing material may be 10 parts, 12 parts, 13 parts, or 15 parts by weight.

The soluble nickel salt refers to a compound that is soluble in water or other solvents to form corresponding nickel ions. In some embodiments, the soluble nickel salt may include at least one of nickel nitrate, nickel sulfate, or nickel chloride. Nickel ions ($Ni^{2+}$) in the nickel salt possess vacant orbitals, which can form coordination bonds with atoms (such as nitrogen or sulfur) in the odor molecules that have lone electron pairs. For example, for nitrogen-containing odor trimethylamine, $Ni^{2+}$ can adsorb the trimethylamine onto the surface of the porous carrier through coordination interactions, enriching the trimethylamine on a catalyst surface, thereby improving the deodorization efficiency. In addition, in the presence of oxygen, the nickel salt catalyzes an oxidation reaction of the odors. Oxygen molecules are activated to generate highly reactive oxygen species, such as superoxide radicals or hydroxyl radicals. The reactive oxygen species react with the odors adsorbed on the surface, oxidizing the odors into harmless substances such as carbon dioxide, water, and nitrogen. For example, for methyl mercaptan, under catalysis of the nickel salt, the methyl mercaptan is oxidized by the reactive oxygen species into carbon dioxide, water, sulfur dioxide, etc. The sulfur dioxide is further oxidized into stable compounds such as sulfate ions.

In some embodiments, the soluble nickel salt in the adsorptive deodorizing material may be 8 to 9 parts by weight.

In some embodiments, the soluble nickel salt in the adsorptive deodorizing material may be 9 to 10 parts by weight.

In some embodiments, the soluble nickel salt in the adsorptive deodorizing material may be 8 parts, 9 parts, or 10 parts by weight.

The soluble nickel salt synergistically interacts with the soluble copper salt and the manganese compound to enhance the catalytic activity of the adsorptive deodorizing material. In particular, under a high temperature or a complex environmental condition, the stability of the nickel salt helps maintain the deodorizing capability of the adsorptive deodorizing material. In some embodiments of the present disclosure, uniformly distributing the soluble nickel salt throughout the adsorptive deodorizing material provides a sustained catalytic effect.

The phosphoric acid may adjust the acidity and alkalinity of the surface of the porous carrier, enhancing the acidity of the surface of the porous carrier. For alkaline odors, such as the trimethylamine, acidic phosphate groups undergo a neutralization reaction or form interactions such as ionic bonds with the odors, thereby increasing the adsorption capacity of the odors by the porous carrier, accelerating the decomposition and conversion of the odor molecules, and enhancing the deodorizing capability of the adsorptive deodorizing material. In some embodiments, the phosphoric acid is industrial phosphoric acid with a purity of 85%.

In some embodiments, the phosphoric acid in the adsorptive deodorizing material is 10 to 13 parts by weight.

In some embodiments, the phosphoric acid in the adsorptive deodorizing material is 13 to 15 parts by weight.

In some embodiments, the phosphoric acid in the adsorptive deodorizing material is 10 parts, 13 parts, 14 parts, or 15 parts by weight.

In some embodiments of the present disclosure, the phosphoric acid is used to adjust the acidity and alkalinity of the surface of the porous carrier, thereby enhancing the acidity of the surface of the porous carrier. As a result, not only the adsorption capacity of the porous carrier for the alkaline odors is increased, but also the adsorption capacity of the porous carrier for the acidic odors is increased, which accelerates the decomposition and conversion of the odor molecules and enhances the deodorizing capability of the adsorptive deodorizing material.

In some embodiments, the adsorptive deodorizing material includes: in parts by weight, 235 parts of the activated carbon powder, 50 parts of the deionized water, 20 parts of the manganese oxide, 12 parts of the copper chloride, 13 parts of the phosphoric acid, and 9 parts of the nickel nitrate.

In some embodiments, the adsorptive deodorizing material includes: in parts by weight, 240 parts of the activated carbon powder, 55 parts of the deionized water, 25 parts of the manganese chloride, 15 parts of the copper sulfate, 15 parts of the phosphoric acid, and 10 parts of the nickel sulfate.

In some embodiments, the adsorptive deodorizing material includes: in parts by weight, 230 parts of the activated carbon powder, 45 parts of the deionized water, 15 parts of the manganese sulfate, 10 parts of the copper nitrate, 10 parts of the phosphoric acid, and 8 parts of the nickel nitrate.

In some embodiments, the adsorptive deodorizing material has a specific surface area of 1000 to 1500 $m^2/g$.

In some embodiments, the adsorptive deodorizing material has a specific surface area of 1000 $m^2/g$, 1100 $m^2/g$, 1200 $m^2/g$, 1300 $m^2/g$, 1400 $m^2/g$, or 1500 $m^2/g$.

In some embodiments, the adsorptive deodorizing material has a specific surface area of 1000 to 1150 $m^2/g$, 1150 to 1250 $m^2/g$, 1250 to 1350 $m^2/g$, 1350 to 1450 $m^2/g$, or 1450 to 1500 $m^2/g$.

By setting the specific surface area of the adsorptive deodorizing material within a range of 1000 to 1500 $m^2/g$, the adsorptive deodorizing material maintains an excellent adsorption capacity. The adsorptive deodorizing material also maintains a high strength. During actual use, the adsorptive deodorizing material is not prone to breakage, pulverization, etc.

In some embodiments, the adsorptive deodorizing material has a porous structure. The porous structure provides a relatively large specific surface area, which is conducive to adsorption of the air molecules.

In some embodiments, the adsorptive deodorizing material has a honeycomb structure. The honeycomb structure provides the adsorptive deodorizing material with a larger specific surface area and more active sites. The honeycomb structure increases a contact area between the adsorptive deodorizing material and an air or a liquid, effectively capturing and adsorbing the odors. Thus, adsorption efficiency is improved.

In some embodiments, the adsorptive deodorizing material is granular or spherical particles, which facilitates packaging and use. The interparticle voids also facilitate the gas flow and adsorption.

FIG. 1 is a flowchart illustrating an exemplary preparation method for an adsorptive deodorizing material according to some embodiments of the present disclosure.

In some embodiments, the preparation method for the adsorptive deodorizing material includes: stirring and mixing deionized water, a manganese compound, a soluble copper salt, phosphoric acid, and a soluble nickel salt in a stirrer to obtain a chemical agent; spraying 40% to 60% of a total mass of the chemical agent onto activated carbon powder, stirring and mixing, placing the activated carbon powder mixed with the 40% to 60% of the total mass of the chemical agent into a mold for molding, and sintering after molding to obtain a semi-finished adsorptive deodorizing material; soaking the semi-finished adsorptive deodorizing material in a remaining chemical agent; and after soaking, drying the semi-finished adsorptive deodorizing material to obtain the adsorptive deodorizing material.

In some embodiments, as shown in FIG. 1, the preparation method for the adsorptive deodorizing material includes steps S001 to S004.

S001: stirring and mixing 45 to 55 parts of the deionized water, 15 to 25 parts of the manganese compound, 10 to 15 parts of the soluble copper salt, 10 to 15 parts of the phosphoric acid, and 8 to 10 parts of the soluble nickel salt in the stirrer to obtain a chemical agent.

S002: spraying 40% to 60% of a total mass of the chemical agent onto 230 to 240 parts of the activated carbon powder, stirring and mixing, placing the activated carbon powder mixed with the 40% to 60% of the total mass of the chemical agent into the mold for molding, and sintering after molding to obtain a semi-finished adsorptive deodorizing material.

Spraying the chemical agent refers to spraying the chemical agent that is uniformly mixed onto the activated carbon powder.

In some embodiments, the sprayed chemical agent accounts for 40% to 60% of the total mass of the chemical agent.

In some embodiments, the sprayed chemical agent accounts for 40%, 42%, 44%, 46%, 48%, 50%, 52%, 54%, 56%, 58%, or 60% of the total mass of the chemical agent.

In some embodiments, the sprayed chemical agent accounts for 40% to 41%, 40% to 43%, 40% to 45%, 40% to 47%, or 40% to 49% of the total mass of the chemical agent.

In some embodiments, the sprayed chemical agent accounts for 51% to 60%, 53% to 60%, 55% to 60%, or 57% to 60% of the total mass of the chemical agent.

The semi-finished adsorptive deodorizing material refers to an intermediate product during preparation of the adsorptive deodorizing material.

In some embodiments, by first uniformly mixing the activated carbon powder with a portion of the chemical agent, the chemical agent fully penetrates the activated carbon powder. During sintering, high temperature promotes a reaction between the activated carbon and components in the chemical agent to form chemical bonds or strong physical adsorption. Thus, loss of catalyst components in the chemical agent is reduced, and the loading capacity of the catalyst is increased. Meanwhile, the catalyst components are preliminarily fixed and dispersed in the porous carrier of the activated carbon to form catalytic sites with certain activity.

In some embodiments, a proportion of the sprayed chemical agent to the total mass of the chemical agent is 50%.

S003: soaking the semi-finished adsorptive deodorizing material obtained by sintering in a remaining chemical agent.

The remaining chemical agent refers to a chemical agent remaining after spraying onto the activated carbon powder.

In some embodiments, soaking the semi-finished adsorptive deodorizing material in the remaining chemical agent further adjusts a structure of active centers of the catalyst components, thereby enhancing activity of the catalyst and enabling the catalyst to more effectively catalyze the decomposition of harmful components in the odors, thus enhancing the deodorizing capability of the adsorptive deodorizing material. In addition, the phosphoric acid in the chemical agent opens blocked pores in the porous carrier, thereby increasing the specific surface area of the adsorptive deodorizing material.

S004: after soaking, drying the semi-finished adsorptive deodorizing material to obtain the adsorptive deodorizing material.

In some embodiments, a temperature for drying the semi-finished adsorptive deodorizing material is within 80 to 120° C., and a time for drying is within 2 to 4 h.

In some embodiments of the present disclosure, by first uniformly mixing the activated carbon powder with the portion of the chemical agent, molding and sintering the activated carbon powder mixed with the portion of the chemical agent, and soaking in the remaining chemical agent, the catalyst components in the chemical agent form stable bonds with the porous carrier, preventing the adsorptive deodorizing material from being lost or agglomerated during use, thereby enabling the adsorptive deodorizing material to maintain a good deodorizing capability for a long time.

In some embodiments, a molding pressure for the activated carbon powder mixed with the chemical agent is 10 MPa to 20 MPa, a sintering temperature is 800° C. to 850° C., and a sintering time is 7 to 8 h.

In some embodiments, the sintering process is carried out in an inert gas atmosphere. By controlling the sintering to be performed under a protection of an inert gas (e.g., nitrogen or argon), an activated carbon matrix is prevented from contacting oxygen and burning out at a high temperature of 800 to 850° C., thereby preserving an adsorption framework of the adsorptive deodorizing material and active components of loaded metal salts, such as manganese, copper, and nickel.

In some embodiments, the molding pressure for the activated carbon powder mixed with the chemical agent is 15 MPa, the sintering temperature is 800° C., and the sintering time is 8 h.

In some embodiments, the molding pressure for the activated carbon powder mixed with the chemical agent is 20 MPa, the sintering temperature is 850° C., and the sintering time is 7 h.

In some embodiments, the molding pressure for the activated carbon powder mixed with the chemical agent is 10 MPa, the sintering temperature is 800° C., and the sintering time is 8 h.

In some embodiments, the molding pressure for the activated carbon powder mixed with the chemical agent is 10 MPa, 12 MPa, 15 MPa, 18 MPa, or 20 MPa.

In some embodiments, the sintering temperature for the activated carbon powder mixed with the chemical agent is 800° C., 820° C., 840° C., or 850° C.

In some embodiments, the sintering time for the activated carbon powder mixed with the chemical agent is 7 h, 7.5 h, or 8 h.

In some embodiments, a soaking time for the semi-finished adsorptive deodorizing material is 8 to 10 h.

In some embodiments, the soaking time for the semi-finished adsorptive deodorizing material is 8 h, 9 h, or 10 h.

Some embodiments of the present disclosure further provide an air purification device, including the adsorptive deodorizing material. In some embodiments, the air purification device may be a deodorizing box for containing the adsorptive deodorizing material. The deodorizing box is usable in spaces requiring deodorization and purification, such as a refrigerator, a shoe cabinet, and a vehicle interior. The deodorizing box not only improves the quality of life but also contributes to better health. The air purification device is also an air purifier equipped with a filter material, so that the air purification device is configured in laboratories, factories, and other spaces that need to purify air.

To further illustrate the adsorptive deodorizing material and the preparation method provided in the present disclosure, Embodiments 1 to 3 and Comparative embodiments 1 to 4 are provided as follows.

Embodiment 1

In Embodiment 1, an adsorptive deodorizing material includes: in parts by weight, 235 parts of activated carbon powder, 50 parts of deionized water, 20 parts of manganese oxide, 12 parts of copper chloride, 13 parts of phosphoric acid, and 9 parts of nickel nitrate.

In Embodiment 1, the activated carbon powder has a mesh size of 300 mesh.

Embodiment 1 also provides a preparation method for the adsorptive deodorizing material, including following steps.

S101: stirring and mixing 50 parts of the deionized water, 20 parts of the manganese oxide, 12 parts of the copper chloride, 13 parts of the phosphoric acid, and 9 parts of the nickel nitrate in a stirrer to obtain a chemical agent.

S102: spraying 40% of a total mass of the chemical agent onto 235 parts of the activated carbon powder, stirring and mixing, placing the activated carbon powder mixed with the 40% of the total mass of the chemical agent in a mold for molding, and sintering after molding to obtain a semi-finished adsorptive deodorizing material, with a molding pressure of 15 MPa, a sintering temperature of 800° C., and a sintering time of 8 h.

S103: soaking the semi-finished adsorptive deodorizing material obtained by sintering in a remaining chemical agent for 10 h.

S104: after soaking, drying the semi-finished adsorptive deodorizing material to obtain the adsorptive deodorizing material.

A temperature for drying the semi-finished adsorptive deodorizing material is 100° C. and a time for drying the semi-finished adsorptive deodorizing material is 3 h.

Embodiment 2

In Embodiment 2, an adsorptive deodorizing material includes: in parts by weight, 240 parts of activated carbon powder, 55 parts of deionized water, 25 parts of manganese chloride, 15 parts of copper sulfate, 15 parts of phosphoric acid, and 10 parts of nickel sulfate.

In Embodiment 2, the activated carbon powder has a mesh size of 400 mesh.

Embodiment 2 also provides a preparation method for the adsorptive deodorizing material, including following steps.

S201: stirring and mixing 55 parts of the deionized water, 25 parts of the manganese chloride, 15 parts of the copper sulfate, 15 parts of the phosphoric acid, and 10 parts of the nickel sulfate in a stirrer to obtain a chemical agent.

S202: spraying 50% of a total mass of the chemical agent onto 240 parts of the activated carbon powder, stirring and mixing, placing the activated carbon powder mixed with the 50% of the total mass of the chemical agent in a mold for molding, and sintering after molding to obtain a semi-finished adsorptive deodorizing material, with a molding pressure of 20 MPa, a sintering temperature of 850° C., and a sintering time of 7 h.

S203: soaking the semi-finished adsorptive deodorizing material obtained by sintering in a remaining chemical agent for 10 h.

S204: after soaking, drying the semi-finished adsorptive deodorizing material to obtain the adsorptive deodorizing material.

A temperature for drying the semi-finished adsorptive deodorizing material is 100° C. and a time for drying the semi-finished adsorptive deodorizing material is 3 h.

Embodiment 3

In Embodiment 3, an adsorptive deodorizing material includes: in parts by weight, 230 parts of activated carbon powder, 45 parts of deionized water, 15 parts of manganese sulfate, 10 parts of copper nitrate, 10 parts of phosphoric acid, and 8 parts of nickel nitrate.

In Embodiment 3, the activated carbon powder has a mesh size of 200 mesh.

Embodiment 3 also provides a preparation method for the adsorptive deodorizing material, including following steps.

S301: stirring and mixing 45 parts of the deionized water, 15 parts of the manganese sulfate, 10 parts of the copper nitrate, 10 parts of the phosphoric acid, and 8 parts of the nickel nitrate in a stirrer to obtain a chemical agent.

S302: spraying 60% of a total mass of the chemical agent sprayed onto 230 parts of the activated carbon powder, stirring and mixing, placing the activated carbon powder mixed with the 60% of the total mass of the chemical agent in a mold for molding, and sintering after molding to obtain a semi-finished adsorptive deodorizing material, with a molding pressure of 10 MPa, a sintering temperature of 800° C., and a sintering time of 8 h.

S303: soaking the semi-finished adsorptive deodorizing material obtained by sintering in a remaining chemical agent for 10 h.

S304: after soaking, drying the semi-finished adsorptive deodorizing material to obtain the adsorptive deodorizing material.

A temperature for drying the semi-finished adsorptive deodorizing material is 100° C. and a time for drying the semi-finished adsorptive deodorizing material is 3 h.

Comparative Embodiment 1

In Comparative embodiment 1, an adsorptive deodorizing material includes: in parts by weight, 235 parts of activated carbon powder, 50 parts of deionized water, 20 parts of manganese oxide, 12 parts of copper chloride, and 9 parts of nickel nitrate.

In Comparative embodiment 1, the activated carbon powder has a mesh size of 300 mesh.

Comparative embodiment 1 also provides a preparation method for the adsorptive deodorizing material, including following steps.

D101: stirring and mixing 50 parts of the deionized water, 20 parts of the manganese oxide, 12 parts of the copper chloride, and 9 parts of the nickel nitrate in a stirrer to obtain a chemical agent.

D102: spraying 40% of a total mass of the chemical agent onto 235 parts of the activated carbon powder, stirring and mixing, placing the activated carbon powder mixed with the 40% of the total mass of the chemical agent in a mold for molding, and sintering after molding to obtain a semi-finished adsorptive deodorizing material, with a molding pressure of 15 MPa, a sintering temperature of 800° C., and a sintering time of 8 h.

D103: soaking the semi-finished adsorptive deodorizing material obtained by sintering in a remaining chemical agent for 10 h.

D104: after soaking, drying the semi-finished adsorptive deodorizing material to obtain the adsorptive deodorizing material.

A temperature for drying the semi-finished adsorptive deodorizing material is 100° C. and a time for drying the semi-finished adsorptive deodorizing material is 3 h.

Comparative Embodiment 2

In Comparative embodiment 2, an adsorptive deodorizing material includes: in parts by weight, 235 parts of activated carbon powder, 50 parts of deionized water, 20 parts of manganese oxide, 12 parts of copper chloride, 10 parts of phosphoric acid, and 9 parts of nickel nitrate.

In Comparative embodiment 2, the activated carbon powder has a mesh size of 300 mesh.

Comparative embodiment 2 also provides a preparation method for the adsorptive deodorizing material, including following steps.

D201: stirring and mixing 50 parts of the deionized water, 20 parts of the manganese oxide, 12 parts of the copper chloride, 10 parts of the phosphoric acid, and 9 parts of the nickel nitrate in a stirrer to obtain a chemical agent.

D202: spraying 40% of a total mass of the chemical agent onto 235 parts of the activated carbon powder, stirring and mixing, placing the activated carbon powder mixed with the 40% of the total mass of the chemical agent in a mold for molding, and sintering after molding to obtain a semi-finished adsorptive deodorizing material, with a molding pressure of 15 MPa, a sintering temperature of 800° C., and a sintering time of 8 h.

D203: soaking the semi-finished adsorptive deodorizing material obtained by sintering in a remaining chemical agent for 10 h.

D204: after soaking, drying the semi-finished adsorptive deodorizing material to obtain the adsorptive deodorizing material.

A temperature for drying the semi-finished adsorptive deodorizing material is 100° C. and a time for drying the semi-finished adsorptive deodorizing material is 3 h.

Comparative Embodiment 3

In Comparative embodiment 3, an adsorptive deodorizing material includes: in parts by weight, 235 parts of activated carbon powder, 50 parts of deionized water, 20 parts of manganese oxide, 12 parts of copper chloride, 13 parts of phosphoric acid, and 9 parts of nickel nitrate.

In Comparative embodiment 3, the activated carbon powder has a mesh size of 100 mesh.

Comparative embodiment 3 also provides a preparation method for the adsorptive deodorizing material, including following steps.

D301: stirring and mixing 50 parts of the deionized water, 20 parts of the manganese oxide, 12 parts of the copper chloride, 13 parts of the phosphoric acid, and 9 parts of the nickel nitrate in a stirrer to obtain a chemical agent.

D302: spraying 40% of a total mass of the chemical agent onto 235 parts of the activated carbon powder, stirring and mixing, placing the activated carbon powder mixed with the 40% of the total mass of the chemical agent in a mold for molding, and sintering after molding to obtain a semi-finished adsorptive deodorizing material, with a molding pressure of 15 MPa, a sintering temperature of 800° C. and a sintering time of 8 h.

D303: soaking the semi-finished adsorptive deodorizing material obtained by sintering in a remaining chemical agent for 10 h.

D304: after soaking, drying the semi-finished adsorptive deodorizing material to obtain the adsorptive deodorizing material.

A temperature for drying the semi-finished adsorptive deodorizing material is 100° C. and a time for drying the semi-finished adsorptive deodorizing material is 3 h.

Comparative Embodiment 4

In Comparative embodiment 4, an adsorptive deodorizing material includes: in parts by weight, 235 parts of activated carbon powder, 50 parts of deionized water, 20 parts of manganese oxide, 12 parts of copper chloride, 13 parts of phosphoric acid, and 9 parts of nickel nitrate.

In Comparative embodiment 4, the activated carbon powder has a mesh size of 400 mesh.

Comparative embodiment 4 also provides a preparation method for the adsorptive deodorizing material, including following steps.

D401: stirring and mixing 50 parts of the deionized water, 20 parts of the manganese oxide, 12 parts of the copper chloride, 13 parts of the phosphoric acid, and 9 parts of the nickel nitrate in a stirrer to obtain a chemical agent.

D402: spraying 40% of a total mass of the chemical agent onto 235 parts of the activated carbon powder, stirring and mixing, placing the activated carbon powder mixed with the 40% of the total mass of the chemical agent in a mold for molding, and sintering after molding to obtain a semi-finished adsorptive deodorizing material, with a molding pressure of 15 MPa, a sintering temperature of 800° C., and a sintering time of 8 h.

D403: soaking the semi-finished adsorptive deodorizing material obtained by sintering in a remaining chemical agent for 10 h.

D404: after soaking, drying the semi-finished adsorptive deodorizing material to obtain the adsorptive deodorizing material.

A temperature for drying the semi-finished adsorptive deodorizing material is 100° C. and a time for drying the semi-finished adsorptive deodorizing material is 3 h.

Comparative Embodiment 5

In Comparative embodiment 5, an adsorptive deodorizing material includes: in parts by weight, 235 parts of activated carbon powder, 50 parts of deionized water, 20 parts of manganese oxide, 12 parts of copper chloride, 13 parts of phosphoric acid, and 9 parts of nickel nitrate.

In Comparative embodiment 5, the activated carbon powder has a mesh size of 300 mesh.

Comparative embodiment 5 also provides a preparation method for the adsorptive deodorizing material, including following steps.

D501: stirring and mixing 50 parts of the deionized water, 20 parts of the manganese oxide, 12 parts of the copper chloride, 13 parts of the phosphoric acid, and 9 parts of the nickel nitrate in a stirrer to obtain a chemical agent.

D502: placing the activated carbon powder mixed with the chemical agent in a mold for molding, and sintering after molding to obtain a semi-finished adsorptive deodorizing material, with a molding pressure of 15 MPa, a sintering temperature of 800° C., and a sintering time of 8 h.

D503: soaking the semi-finished adsorptive deodorizing material obtained by sintering in the entire chemical agent for 10 h.

D504: after soaking, drying the semi-finished adsorptive deodorizing material to obtain the adsorptive deodorizing material.

A temperature for drying the semi-finished adsorptive deodorizing material is 100° C. and a time for drying the semi-finished adsorptive deodorizing material is 3 h.

Removal rates of the methyl mercaptan and the trimethylamine by the adsorptive deodorizing materials provided in Embodiment 1 to Embodiment 3 and Comparative embodiment 1 to Comparative embodiment 5 were tested respectively according to the provisions of the standard "QB/T 2761-2006 Determination Methods for Purification Effect of Indoor Air Purification Products". Test results are shown in Table 1 and Table 2 below (a test chamber in Table 1 and Table 2 is a 60 L test chamber).

TABLE 1

| | | Test result | | |
|---|---|---|---|---|
| Test pollutant: methyl mercaptan | Contact time | Concentration in blank test chamber ($mg/m^3$) | Concentration in sample test chamber ($mg/m^3$) | Removal rate (%) |
| Embodiment 1 | 8 h | 2.39 | <0.01 | >99.6 |
| Embodiment 2 | 8 h | 2.25 | <0.01 | >99.6 |
| Embodiment 3 | 8 h | 2.21 | <0.01 | >99.6 |
| Comparative embodiment 1 | 8 h | 2.32 | 0.039 | 98.3 |
| Comparative embodiment 2 | 8 h | 2.38 | 0.036 | 98.5 |
| Comparative embodiment 3 | 8 h | 2.35 | 0.08 | 96.7 |

TABLE 1-continued

| Test pollutant: methyl mercaptan | Contact time | Test result: Concentration in blank test chamber ($mg/m^3$) | Concentration in sample test chamber ($mg/m^3$) | Removal rate (%) |
|---|---|---|---|---|
| Comparative embodiment 4 | 8 h | 2.37 | 0.10 | 95.8 |
| Comparative embodiment 5 | 8 h | 2.33 | 0.15 | 93.6 |

TABLE 2

| Test pollutant: trimethylamine | Contact time | Test result: Concentration in blank test chamber ($mg/m^3$) | Concentration in sample test chamber ($mg/m^3$) | Removal rate (%) |
|---|---|---|---|---|
| Embodiment 1 | 8 h | 2.07 | 0.0202 | 99.0 |
| Embodiment 2 | 8 h | 2.12 | 0.0207 | 99.3 |
| Embodiment 3 | 8 h | 2.03 | 0.0162 | 99.2 |
| Comparative embodiment 1 | 8 h | 2.14 | 0.1327 | 93.8 |
| Comparative embodiment 2 | 8 h | 2.04 | 0.0898 | 95.6 |
| Comparative embodiment 3 | 8 h | 2.08 | 0.0874 | 95.8 |
| Comparative embodiment 4 | 8 h | 2.12 | 0.0848 | 96.0 |
| Comparative embodiment 5 | 8 h | 2.06 | 0.11 | 94.7 |

According to the test results of Embodiments, Comparative embodiments, and Table 2, the removal rates of the trimethylamine by the adsorptive deodorizing materials provided in Comparative embodiment 1 and Comparative embodiment 2 are 93.8% to 95.6%, which are significantly lower than the removal rates of the trimethylamine by the adsorptive deodorizing materials provided in Embodiment 1 to Embodiment 3 (99.0% to 99.3%). This is because the acidity on the surface of the porous carrier in the adsorptive deodorizing materials provided in Comparative embodiment 1 and Comparative embodiment 2 is relatively weak. For example, the phosphoric acid is not added in the adsorptive deodorizing material provided in Comparative embodiment 1. The adsorptive deodorizing material provided in Comparative embodiment 2 has a low parts by weight of the phosphoric acid. Consequently, the acidity on the surface of the porous carrier is relatively weak. The adsorption effect on the trimethylamine of the porous carrier in the adsorptive deodorizing materials provided in Comparative embodiment 1 and Comparative embodiment 2 is weaker than that of the porous carrier in the adsorptive deodorizing materials provided in Embodiment 1 to Embodiment 3. It can be seen that, in some embodiments of the present disclosure, the acidity and basicity on the surface of the porous carrier are adjusted by introducing the phosphoric acid. The spraying amount of the chemical agent onto the activated carbon powder is controlled. The acidity on the surface of the porous carrier is ensured to be within a reasonable numerical range. The removal rate of the trimethylamine by the adsorptive deodorizing material is significantly improved.

According to the test results of Embodiments, Comparative embodiments, Table 1, and Table 2, the removal rates of the methyl mercaptan by the adsorptive deodorizing materials provided in Comparative embodiment 3 and Comparative embodiment 4 are 95.8% to 96.7%, which are significantly lower than the removal rates of the methyl mercaptan by the adsorptive deodorizing materials provided in Embodiment 1 to Embodiment 3 (>99.6%). The removal rates of the trimethylamine by the adsorptive deodorizing materials provided in Comparative embodiment 3 and Comparative embodiment 4 are 95.8% to 96.0%, which are significantly lower than the removal rates of the trimethylamine by the adsorptive deodorizing materials provided in Embodiment 1 to Embodiment 3 (99.0% to 99.3%). This is because the air permeability of the porous carrier in the adsorptive deodorizing materials provided in Comparative embodiment 3 and Comparative embodiment 4 is low. The adsorption capacity of the porous carrier for odors is inferior to that of the porous carrier in the adsorptive deodorizing materials provided in Embodiment 1 to Embodiment 3. It can be seen that, in some embodiments of the present disclosure, by setting the particle size of the activated carbon powder in the adsorptive deodorizing material within 200 to 400 mesh, the air permeability of the porous carrier is improved, thereby significantly enhancing the removal rates of the methyl mercaptan and the trimethylamine by the adsorptive deodorizing material.

According to the test results of Embodiments, Comparative embodiments, Table 1, and Table 2, 8-hour removal rates of the methyl mercaptan and the trimethylamine in Comparative embodiment 5 are 93.6% and 94.7%, respectively, which are significantly lower than those in Embodiment 1 to Embodiment 3 (all >99%). It can be seen that when the adsorptive deodorizing material is subjected only to overall soaking after sintering, without prior spraying or partial fixation of the catalyst, the active components cannot form stable and efficient acidic or catalytic sites on the carrier surface. Moreover, this may cause partial pore blockage or uneven distribution of the active components, thereby leading to a decline in adsorption and catalytic performance. Based on this comparison, first spraying a portion of the chemical agent to achieve preliminary fixation, the activated carbon powder can be uniformly mixed with the portion of the chemical agent before subsequent molding, sintering, and soaking, which helps achieve a higher removal efficiency.

The foregoing descriptions are merely preferred embodiments of the present disclosure and do not in any way limit the patent scope of the present disclosure. Any equivalent structural variations made based on the concepts of the present disclosure, or any direct or indirect applications in other related technical fields using the content of the present disclosure and the accompanying drawings, are all encompassed within the protection scope of the present disclosure.

What is claimed is:

1. An adsorptive deodorizing material, comprising: in parts by weight, 230 to 240 parts of activated carbon powder, 45 to 55 parts of deionized water, 15 to 25 parts of a manganese compound, 10 to 15 parts of a soluble copper salt, 10 to 15 parts of phosphoric acid, and 8 to 10 parts of a soluble nickel salt;

wherein the phosphoric acid is industrial phosphoric acid with a purity of 85%;

the activated carbon powder has a mesh size of 240-400 mesh;

the adsorptive deodorizing material has a specific surface area of 1000-1500 $m^2/g$; and the adsorptive deodorizing material is prepared by a process including:

stirring and mixing the deionized water, the manganese compound, the soluble copper salt, the phosphoric acid, and the soluble nickel salt to obtain a chemical agent;

spraying 40%-60% of a total mass of the chemical agent onto the activated carbon powder, stirring and mixing, placing the activated carbon powder mixed with the 40%-60% of the total mass of the chemical agent into a mold for molding, and performing a sintering step after molding to obtain a semi-finished adsorptive deodorizing material;

soaking the semi-finished adsorptive deodorizing material in a remaining portion of the chemical agent; and drying the semi-finished adsorptive deodorizing material after soaking to obtain the adsorptive deodorizing material.

2. The adsorptive deodorizing material according to claim 1, wherein the manganese compound includes at least one of manganese oxide, manganese chloride, or manganese sulfate.

3. The adsorptive deodorizing material according to claim 1, wherein the soluble copper salt includes at least one of copper chloride, copper sulfate, or copper nitrate.

4. The adsorptive deodorizing material according to claim 1, wherein the soluble nickel salt includes at least one of nickel nitrate, nickel sulfate, or nickel chloride.

5. The adsorptive deodorizing material according to claim 1, comprising: in parts by weight, 235 parts of the activated carbon powder, 50 parts of the deionized water, 20 parts of manganese oxide, 12 parts of copper chloride, 13 parts of the phosphoric acid, and 9 parts of nickel nitrate.

6. The adsorptive deodorizing material according to claim 1, comprising: in parts by weight, 240 parts of the activated carbon powder, 55 parts of the deionized water, 25 parts of manganese chloride, 15 parts of copper sulfate, 15 parts of the phosphoric acid, and 10 parts of nickel sulfate.

7. The adsorptive deodorizing material according to claim 1, comprising: in parts by weight, 230 parts of the activated carbon powder, 45 parts of the deionized water, 15 parts of manganese sulfate, 10 parts of copper nitrate, 10 parts of the phosphoric acid, and 8 parts of nickel nitrate.

8. The adsorptive deodorizing material according to claim 1, wherein the activated carbon powder has a mesh size of 300 mesh.

9. The adsorptive deodorizing material according to claim 1, wherein the adsorptive deodorizing material has a honeycomb structure.

10. The adsorptive deodorizing material according to claim 1, wherein the sintering step is performed in an inert gas atmosphere.

11. The adsorptive deodorizing material according to claim 1, wherein components of the manganese compound, the soluble copper salt, the phosphoric acid, and the soluble nickel salt form chemical bonds or strong physical adsorption with the activated carbon powder during sintering.

12. The adsorptive deodorizing material of claim 1, wherein the adsorptive deodorizing material is in a form of granular or spherical particles.

* * * * *